United States Patent [19]

Hiiro et al.

[11] 4,168,219
[45] Sep. 18, 1979

[54] ELECTRODE FOR MEASUREMENT OF IONIC ACTIVITY, SENSOR FILM THEREFOR AND METHOD FOR MANUFACTURE THEREOF

[75] Inventors: Kazuo Hiiro, Kawanishi; Akinori Kawahara, Ikeda; Takashi Tanaka, Kyoto, all of Japan

[73] Assignee: Agency of Industrial Science & Technology, Ministry of International Trade & Industry, Tokyo, Japan

[21] Appl. No.: 891,175

[22] Filed: Mar. 29, 1978

[30] Foreign Application Priority Data

Apr. 4, 1977 [JP] Japan .................................... 52-38843
Jun. 27, 1977 [JP] Japan .................................... 52-76718

[51] Int. Cl.² ............................................. G01N 27/30
[52] U.S. Cl. .................................. 204/195 M; 427/58
[58] Field of Search ............. 204/195 M, 1 T; 324/29; 427/58

[56] References Cited
U.S. PATENT DOCUMENTS
3,843,505  10/1974  Higuchi ............................. 204/195 M Primary Examiner—G. L. Kaplan
Attorney, Agent, or Firm—Oblon, Fisher, Spivak, McClelland & Maier

[57] ABSTRACT

An electrode for the measurement of ionic activity, having a sensor film made preponderantly of a substance sensitive to the ion subjected to measurement and Urushi (Japanese lacquer). The sensor film of said electrode is manufactured by a method which comprises mixing the aqueous solution of said sensitive substance with Urushi (Japanese lacquer), molding the resultant mixture and causing the molded mixture to set.

10 Claims, 12 Drawing Figures

Fig_3

Fig_6

Fig_4

Fig_8

ELECTRODE FOR MEASUREMENT OF IONIC ACTIVITY, SENSOR FILM THEREFOR AND METHOD FOR MANUFACTURE THEREOF

BACKGROUND OF THE INVENTION

This invention relates to an electrode incorporating a novel sensor film and used for the measurement of the activity of an ion in a solution, and to a method for the manufacture of said sensor film.

Generally the activity of an ion in a solution is measured by the following method.

A reference electrode and an electrode designed for the measurement of ionic activity are immersed and opposed to each other in a solution under test and the potential difference between these two electrodes is measured, whereby the activity of the ion in the solution is determined on the basis of the measured value of said potential difference.

Now, the construction of a typical liquid film type electrode designed for the measurement of ionic activity will be described below.

A porous thin film formed of a chemically stable substance is attached over the opening at the bottom of a tubular electrode body. Inside the body is placed an internal solution and an organic ion-exchange liquid which acts as a sensitive substance. This latter mentioned liquid is a substance which is immiscible with the solution under test and which when held in direct contact with said solution, induces the phenomenon of ion exchange along the interface. This liquid permeates the porous thin film so that when the electrode is immersed in a given solution for the purpose of measurement, the solution under test and the internal solution of the electrode come into mutual contact through the medium of the organic ion-exchange liquid.

The electrode disclosed in Japanese Patent Publication No. 14678/1969, (U.S. Ser. No. 390016, filed Aug. 17, 1964, now U.S. Pat. No. 3,429,785) the Model 92 electrode made by Orion Corp. of the United States, the Model 476114 electrode made by Corning Corp. of the United States, etc. are all electrodes of the construction described above, designed for the measurement of ionic activity.

These electrodes have disadvantages such as are indicated below.

1. It is impossible to completely prevent the organic ion-exchange liquid from passing through the porous thin film and entering into the solution under test.

For this reason, the organic ion-exchange liquid must be kept under constant watch during the service of the electrode and must be replenished to make up for the loss due to the escape into the solution.

2. The escape of the organic ion-exchange liquid into the solution under test entails a degradation in the accuracy of measurement.

3. Where the solution subjected to measurement contains an organic solvent such as alcohol, the organic ion-exchange liquid and the solution are dissolved into each other, making the measurement impossible.

4. The electrode construction is complicated. The electrode made by Orion Corp., for example, is composed of a portion filled with the organic ion-exchange liquid, a portion filled with the internal solution of the electrode, a portion serving to retain in position the porous thin film, an internal electrode, etc. Besides, the electrode is required to be constructed so as to permit replacement of the organic ion-exchange liquid or porous thin film. For these reasons, the electrode is manufactured at a great cost.

5. The porous thin film has insufficient mechanical strength. If the solution under test happens to contain any floating matter, there is a possibility that the thin film will sustain injuries. The solution under test is normally kept in a stirred condition during the measurement in order to ensure high accuracy of the measurement. The resulting agitation of the solution, however, causes vibration of the thin film and accordingly prevents the electrode from registering results with high consistency.

6. Because of deterioration, the thin film must be replaced with a new one at certain intervals. The detachment of the old film and the attachment of the new film require high skill on the part of the operator.

All the defects enumerated above originate from the fact that a porous thin film is used as the sensitive film.

To overcome these drawbacks, there have been proposed and accepted for actual use improved sensitive films such as, for example, a film supported on a porous carrier made of colloidal silica and a film produced by mixing a liquid sensitive substance with a synthetic polymer like an epoxy resin or silicone rubber, molding the resultant mixture and causing the molded mixture to set.

In the former film, although the mechanical strength is improved to some extent, the other defects still persist.

The latter film is difficult to manufacture and possesses insufficient mechanical strength and, because the film surface is not smooth and the film texture is not hard, the film provides a short service life and fails to maintain its precision of measurement stably for a long time.

An object of the present invention is to provide an electrode for the measurement of ionic activity, which enjoys high mechanical strength, provides a long service life, permits measurement of various kinds of ions and excels in precision of measurement.

Another object of the present invention is to provide a method for the manufacture of a sensor film for the electrode to be used for the measurement of ionic activity, which electrode enjoys high mechanical strength, provides a long service life, permits measurement of various kinds of ions and excels in precision of measurement.

BRIEF SUMMARY OF THE INVENTION

To accomplish the objects described above according to the present invention, there is provided an electrode for the measurement of ionic activity, which electrode incorporates a sensor film formed of a substance sensitive to the ion subjected to measurement and Urushi (Japanese lacquer) at a mixing weight ratio of from 0.1 to 0.97 of Urushi (Japanese lacquer) to 1 of the entire mixture consisting of a liquid sensitive substance or the solution of a sensitive substance and Urushi (Japanese lacquer). The sensor film is produced by homogeneously mixing Urushi (Japanese lacquer) with said liquid sensitive substance or a solution obtained by dissolving a sensitive substance with an organic solvent and causing the resultant mixture to set.

DETAILED DESCRIPTION OF THE INVENTION

The electrode of the present invention for the measurement of ionic activity will be described with reference to FIG. 1 which illustrates a typical preferred embodiment of said electrode.

A glass tube 1 has a metallic base 2 attached to one end thereof. On the outside bottom of said metallic base 2, there is deposited a sensor film 3 which is formed by applying to said bottom a pasty mixture consisting of Urushi (Japanese lacquer) and a liquid sensitive substance or the solution of a sensitive substance in an organic solvent (sensitive relative to the ion subjected to measurement) and causing the applied pasty mixture to set. The center wire of a shielded coaxial wire 4 passing along the center of the glass tube 1 is connected to the metallic base 2 by a mass of solder 5. The other end of this wire is connected at a junction 7 with the center wire of another coaxial shielded wire 6 which leads to a system for the measurement of electrode potential (not shown). An adhesive agent 8 and an insulator 9 serve to immobilize said shielded wire 4 and the junction 7 relative to the glass tube 1. Said sensor film 3 is composed preponderantly of a substance sensitive to the ion subjected to the measurement and Urushi (Japanese lacquer) and may also contains an organic solvent. The mixing ratio of the sensitive substance, Urushi (Japanese lacquer) and organic solvent is 0.03 to 0.9: 0.1 to 0.97: 0.0 to 0.9 respectively by weight on the basis of the entire mixture taken as 1. The reason for the limits on the weight ratio is as follows: If Urushi (Japanese lacquer) is used in an excess amount, the weight proportion of the substance sensitive to the ion subjected to the measurement is too small for the produced electrode to fulfil its function sufficiently. If Urushi (Japanese lacquer) is used in an insufficient amount, there is a possibility that when the pasty mixture will not be allowed to set amply or will fail to set at all.

As will be fully appreciated in the course of the actual manufacture of the electrode, incorporation of an organic solvent in a weight proportion of 0.1 to 0.9 into the pasty mixture results, more often than not, in an improvement in the properties of the electrode.

As the sensitive substance, there is used a compound containing the same ion as that which is subjected to the measurement. If this sensitive substance happens to be in a solid state, it is dissolved in an organic solvent. It it is in a liquid state from the beginning, no such solution is required. The sensitive substance, either in its prepared form of solution or in its unaltered liquid form, is mixed homogeneously with Urushi (Japanese lacquer) and left to undergo a subsequent hardening reaction. Consequently, there is produced a solid solution having said sensitive substance distributed throughout the matrix of Urushi (Japanese lacquer). Eventually, it amply solidifies and serves as a sensor film enjoying high precision of measurement. Examples of the combinations between sensitive substances and solutions suitable for the measurement are shown below.

| Sensitive substance | Solution for test |
| --- | --- |
| Tri-n-octyl-methyl ammonium nitrate | Sodium nitrate, potassium nitrate, ammonium nitrate |
| Dipicrylamine potassium salt | Potassium nitrate, potassium chloride, potassium sulfate |
| Tri-n-octyl-methyl ammonium iodide | Sodium iodide, potassium iodide, ammonium iodide |
| Tetraphenyl-ammonium-tetrafluoroborate | Sodium tetrafluoroborate, tetrafluoroboric acid, ammonium tetrafluoroborate |
| Tri-n-octylmethyl ammonium chloride | Sodium chloride, potassium chloride, ammonium chloride |
| Tris-(4,7-diphenyl-1,10-phenanthroline)-iron(II)-hexafluorophosphate | Hexafluorophosphoric acid, sodium hexafluorophosphate |
| Tri-n-octyl-methyl ammonium bromide | Sodium bromide, potassium bromide |
| Tri-n-octyl-methyl ammonium perchlorate | Sodium perchlorate, potassium perchlorate |
| Tetraphenyl-phosphonium chromate | Potassium chromate, sodium chromate |
| Tri-dodecyl-hexadecyl-ammonium nitrate | Sodium nitrate, potassium nitrate |
| Tetraphenyl-phosphonium nitrate | Sodium nitrate, potassium nitrate |
| Tri-n-octyl-methyl ammonium chlorate | Sodium chlorate, potassium chlorate |
| Tri-n-octyl-methyl ammonium thiocyanate | Potassium thiocyanate, ammonium thiocyanate |
| Calcium (magnesium) di-2-ethylhexylphosphate | Calcium (magnesium) chloride, calcium (magnesium) nitrate |
| N-lauryl-N-trialkyl-methyl amine cyanide | Sodium cyanide, potassium cyanide |
| Potassium valinomycin | Potassium nitrate, potassium sulfate, potassium chloride |
| Potassium tetraphenylborate | Potassium sulfate, potassium nitrate, potassium chloride |
| Calcium didecylphosphate | Calcium chloride, calcium nitrate |
| Methylene blue-thiocyanate | Potassium thiocyanate, ammonium thiocyanate |
| Tris-(1,10-phenanthroline)-iron(II)-iodide | Potassium iodide, sodium iodide |
| Tris-(1,10-phenanthroline)-iron(II)-tetrafluoroborate | Sodium tetrafluoroborate, tetrafluoroboric acid, ammonium tetrafluoroborarte |

The sensitive substance may be dissolved in an organic solvent such as, for example, nitrobenzene, 1-decanol, 1,2-dichloroethane, chlorobenzene, bromobenzene, glycerol, p-nitrocumene, dinitroethane, dioctylphthalate, n-octyl-2-nitrophenol ether, dioctylphenyl phosphonate, or dodecyl alcohol and, in the form of the resultant solution, mixed with Urushi (Japanese lacquer).

Urushi (Japanese lacquer) is a natural resin which is obtained from various trees such as, for example, a deciduous tree Rhus vernicifera DC and trees of genus Rhus of Family Urushi. The resin is composed of 50 to 80% of urushiol, 10 to 30% of water, 2 to 20% of rubber substance and 1 to 3% of a nitrogen-containing substance and is stored in the form of slurry.

The Urushi (Japanese lacquer) which is used in the present invention need not be particularly limited to any specific species distinguished by place of production or method of production. Any Urushi (Japanese lacquer), no matter whether it is naturally produced or artificially prepared, is acceptable for use in this invention insofar as it contains urushiol. The type of Urushi (Japanese lacquer) which contains rubbery substance and nitrogen-containing substance in relatively large amounts and abounds with a component like laccase capable of accelerating the setting of the pasty mixture is used advantageously because it has a high setting rate.

Now, the manufacture of the sensor film 3 illustrated in FIG. 1 will be described. As the first step, a sensitive substance which is liquid at normal room temperature or dissolved in an organic solvent and Urushi (Japanese lacquer) are prepared. The Urushi (Japanese lacquer) is used in its liquid (slurry) state. Actually, it is stored in a tightly sealed container such as a syringe or tube. At the time of use, it is extruded in a required amount from the syringe or tube. Although the mixing ratio of the sensitive substance and the Urushi (Japanese lacquer) is variable over a wide range, the proportion of the Urushi (Japanese lacquer) is generally in the range of from 0.1 to 0.97 g, preferably from 0.4 to 0.8 g, per g. of the combined amount of said sensitive substance in the form of a liquid or solution and the Urushi (Japanese lacquer). The Urushi (Japanese lacquer) and the sensitive substance are thoroughly mixed. Then, the resultant mixture is applied to the metallic base 2 as shown in FIG. 1 and is allowed to set under proper conditions generally adopted for the setting of Urushi (Japanese lacquer). For example, this setting may be accomplished by naturally drying the applied mixture through ample exposure to the ambient air or thermally drying it in a chamber called an "urushi room", wherein it is left to stand under controlled conditions of from 20 to 30° C. of temperature and from 70 to 80% of relative humidity. When thoroughly set consequently, said mixture converts into a black solid having a surface which glistens as if it were polished. Thus is produced an electrode of this invention which is used for the measurement of ionic activity.

The electrode obtained as described above is immersed in conjunction with a reference electrode such as, for example, a calomel electrode in a solution to be tested. Now by using a known apparatus and following a known procedure, the potential difference between the two electrodes is measured and the activity of the relevant ion present in said solution is determined according to the measured value of the potential.

Owing to the use of the sensor film having the solidified Urushi (Japanese lacquer) as its matrix, the electrode of the present invention for use in the measurement of ionic activity has many effects as indicated below.

Firstly, the sensor film in the electrode of this invention is very easy to produce. It is obtained by a simple procedure of mixing the sensitive substance with Urushi (Japanese lacquer), applying the resultant mixture and allowing the applied mixture to set.

Secondly, the sensor film in the electrode of the invention has a beautiful, richly glossy surface and excels in surface properties for a sensor film. The surface properties are such that otherwise possible deposition of suspended particles on the electrode surface does not occur even when the electrode is subjected to prolonged use.

Thirdly, the sensor film in the electrode of this invention has ample tenacity and solidity so that, unlike the countertype in the conventional electrode, it never allows the sensitive substance to dissolve out of the film into the solution.

Fourthly, the sensitivity of the sensor film for the measurement of ionic activity is not degraded because the sensor film has absolutely no possibility of defiling the solution under test.

Fifthly, the sensor film produced by this invention has an advantage that it can be used even in a solution containing an organic solvent.

Figures 1, 2, 5:
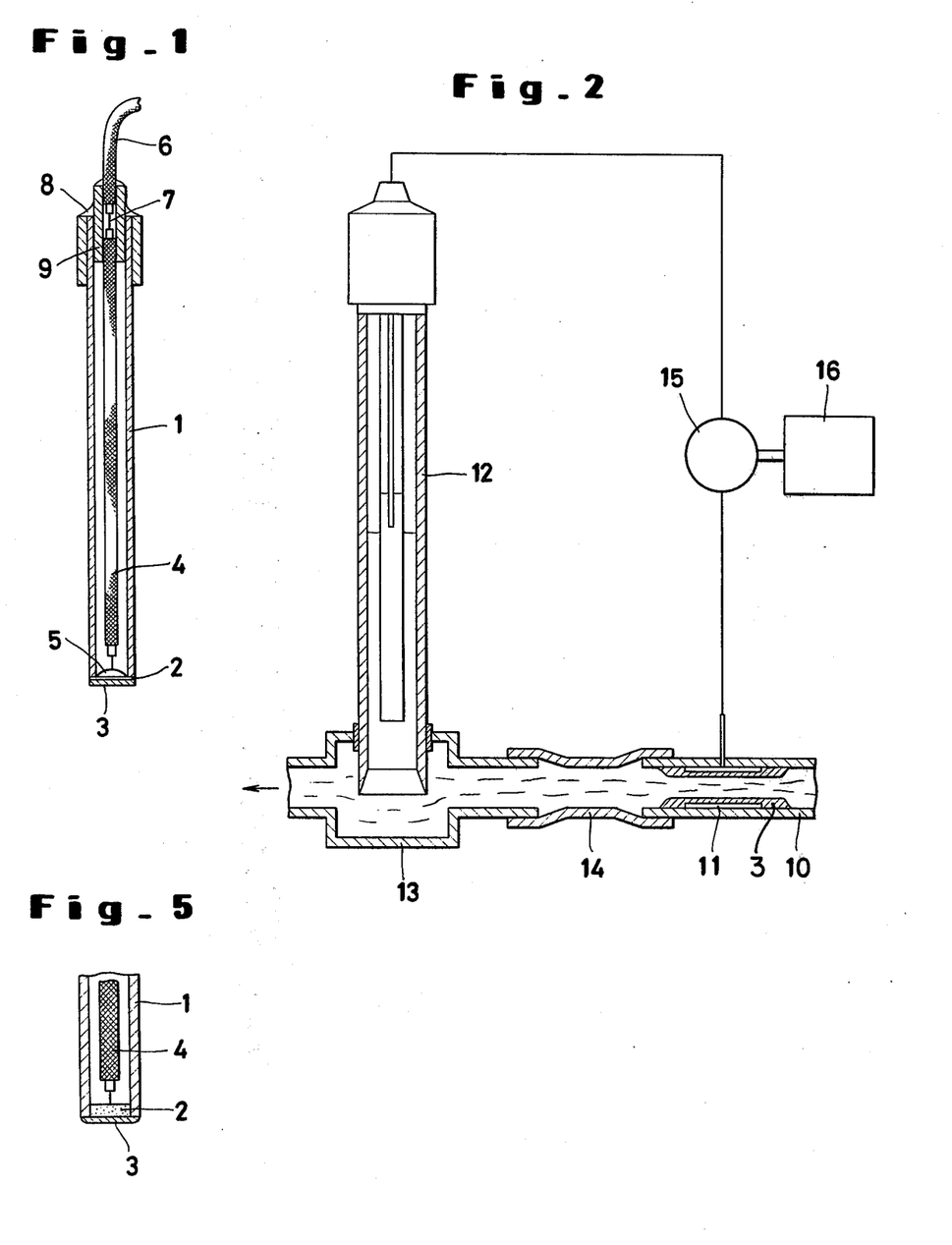
FIG. 1 is a diagram illustrating a typical preferred embodiment of the electrode of this invention for the measurement of ionic activity.
FIG. 2 and FIG. 3 illustrate applications of the electrode of the present invention for the measurement of ionic activity.
FIG. 5 is a diagram illustrating a modification of the construction of the electrode involved in Example 2.

Sixthly, the electrode produced by the present invention has a very simple construction as is evident from the diagram of FIG. 1 so that it hardly experiences mechanical trouble and is inexpensive. Besides, this electrode has no need for an internal solution.

Seventhly, the sensor film in the electrode of this invention excels in mechanical strength. Thus it has no possibility of being injured or vibrated by the flow of the solution under test but stably registers the potential being generated between the two electrodes.

Eighthly, the electrode of this invention provides lasting service without requiring change of a worn sensor film with a new one because the film has high mechanical strength and very rarely sustains breakage. Thus, the operator is not required to possess any appreciable skill in the handling of the electrode.

The electrode of the present invention which enjoys all these merits is manufactured easily and, when used for the measurement of ionic activity, manifests many outstanding properties.

Now, applications of the electrode of this invention to actual measurement of ionic activity will be described with reference to the diagrams of FIG. 2 and FIG. 3. FIG. 2 represents a tubular electrode. Inside a pipe made of glass or plastic material, a metallic base is fixed and a sensor film is formed on the metallic base. In the diagram of FIG. 2, 10 denotes a pipe made of glass or plastic material, 11 a metallic base, 3 a sensor film, 12 a reference electrode, 13 a flow cell for said reference electrode, 14 an insulating rubber or PVC pipe for connecting said flow cell and the glass or plastic pipe 10, 15 a potentiometer for measuring the electrode potential and 16 a recording device. As the solution under test flows through the glass or plastic pipe 10 incorporating the sensor film 3, the pipe 14 and the flow cell 13, it simultaneously comes into contact with the sensor film 3 and the reference electrode 12. Consequently, the potential difference corresponding to the concentration of the objective component in the solution under test is displayed on the potentiometer 15 and recorded on the recording device 16.

Figure 3:
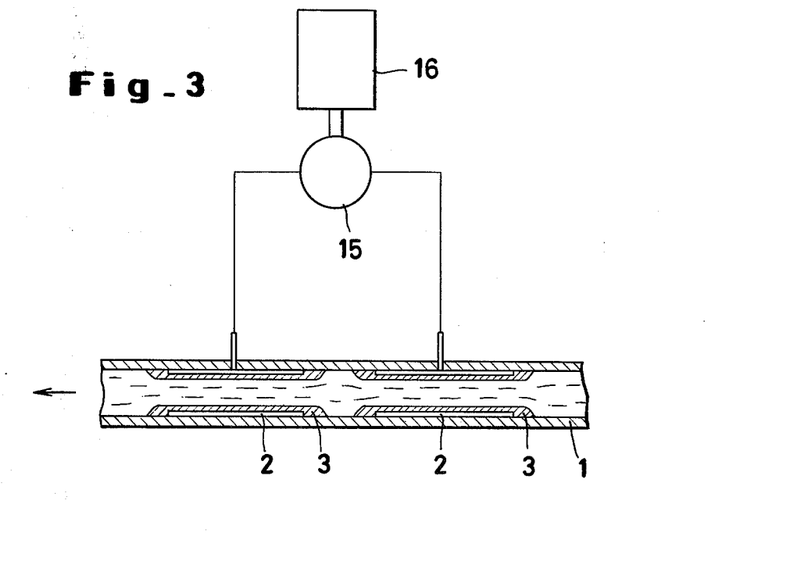

FIG. 3 represents an electrode of further improved shape. In this diagram, 1 denotes a pipe made of glass or plastic material and 2 a pair of metallic bases fixed inside the pipe. Sensor films 3 are formed on the metallic bases. The metallic bases 2 are connected to a potentiometer 15 as illustrated. The value of the measured potential difference is recorded on a recording device 16. In this construction, as the solution under test flows through the interior of the pipe 1, it simultaneously comes into contact with the two sensor films 3. The potential difference between the two sensor films is measured on the potentiometer 15. In this construction, therefore, two electrodes of identical construction are formed and one of them is used as the reference electrode. When this twin electrode is used for measuring the nitric acid ion concentration in sea water, for example, since the chloride ion concentration of sea water is always constant, a sensor film capable of responding to nitric acid ion may be used in one of the two component electrodes formed as described above and a sensor film capable of responding to chloride ion in the other component electrode, so that the electrode with the sensor film responding to the chloride ion registers a constant potential and, therefore, fulfils the part of a reference electrode.

Now, the present invention will be described with reference to working examples.

EXAMPLE 1

A substance sensitive to perchlorate ion was prepared by thoroughly mixing 0.045 g of an ion-exchange liquid #477359 for use in the electrode Model 476114 made by Corning of the United States for the measurement of perchlorate ion (containing a high molecular organic perchlorate compound as one component) with 0.055 g of Ise Urushi (Japanese lacquer) (made by Nishizawa Urushi Hompo of Uehon-machi, Tennoji-ku, Osaka; containing 70% by weight of urushiol, 7% of rubber substance, 2% of nitrogen containing substance and 21% of water). A circular plate of copper about 0.5 mm in thickness and about 11 mm in diameter was attached to one end of a glass tube about 12 mm in outside diameter and about 120 mm in length. A shielded wire was laid through the interior of the glass tube and was soldered at one end to the inner side of said copper circular plate. This small circular plate was fastened to the glass tube through the medium of a silicone rubber type adhesive agent. The aforementioned mixture was applied to the outer side of the small circular plate. The applied mixture was dried by causing the glass tube to be rotated slowly about its longitudinal axis overnight in a room maintained at 60° C. Thereafter, said mixture was again applied and left to dry overnight in the same manner as above. Thus, the sensor film was dried and set. Consequently, there was completed an electrode of a construction like the one illustrated in FIG. 1.

Figure 4:
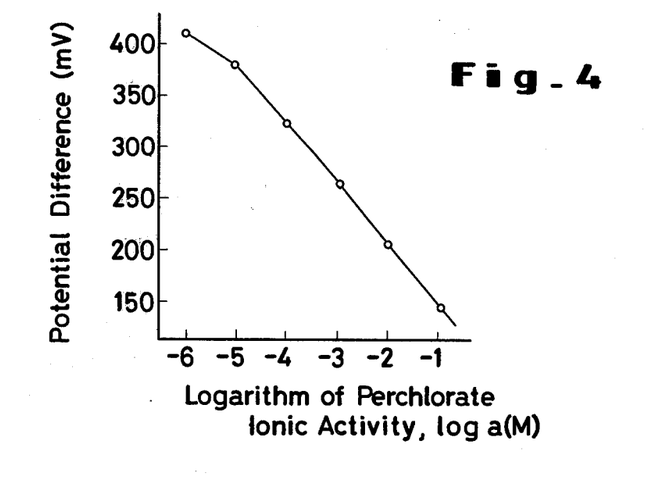
FIG. 4 is a graph showing the results obtained in Example 1.

This electrode was used to measure the potential difference in sodium perchlorate solutions of varying activity. As the reference electrode in this measurement, there was used a double-junction reference electrode Model 92-02-00 made by Orion Corp. of the United States. As the apparatus for the measurement, there was used a digital ion meter Model 801 made by Orion Corp. As is plain from the FIG. 4, the electrode manufactured in accordance with the present invention showed a linear relation between the logarithm of ionic activity and the potential difference within the range of from $10^{-1}$ to $10^{-5}$ M of perchlorate ion activity. For an increase of the perchlorate ion activity by ten times the original value, the change in the potential difference was about 57 mV. The interval between the time the electrode was immersed in the perchlorate ion solution and the time the electrode began to register a constant potential was no more than several seconds, regardless of the magnitude of the ion activity of the perchlorate.

EXAMPLE 2

By following the procedure of Example 1, mixtures of said ion-exchange liquid with said Urushi (Japanese lacquer) were prepared as substances sensitive to perchlorate ion. In this example, the mixing weight ratios of the two components were varied to 3.5:6.5, 4:6, 4.5:5.5, 5:5 and 6:4. In this example, the electrodes were made in a modified construction like the one shown in FIG. 5: In each electrode, minute grooves were cut on the inside wall at the lower end of the glass tube 1. Then about 5 g of a lead alloy was fused on a flat plate and the glass tube 1 was vertically brought down onto said flat plate so that its lower end embraced the pool of fused lead alloy. The alloy lodged at the lower end of the glass tube was left to cool off and solidify. Then the portion of the solidified alloy which was protruding from the lower edge of the glass tube was rubbed off with sandpaper. Consequently, there was obtained a metallic base 2 which was tightly secured after the manner of a stopper to the inside wall of the glass tube. A shielded wire was disposed in advance at a proper position inside the glass tube, so that when the molten lead alloy cooled off and solidified, the bored end of said shielded wire was stuck into the metallic base. By repeating the procedure of Example 1, each mixture of said ion-exchange liquid and said Urushi (Japanese lacquer) was applied to the metallic base 2 and dried and set, giving rise to a sensor film 3. The remaining portions of the electrode such as electrode joint which are not shown in FIG. 5 were the same as those of FIG. 1.

Figure 6:
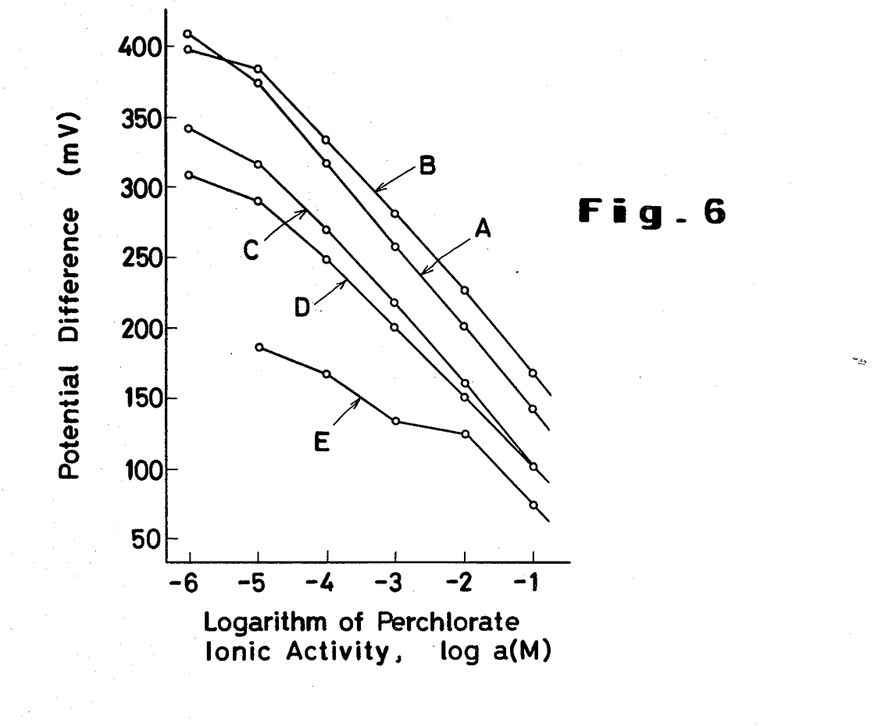
FIG. 6 is a graph showing the results obtained in Example 2.

FIG. 6 graphically shows the results of the measurement performed in this example.

In the graph, A denotes a calibration curve showing the relation between the perchlorate ion activity and the potential difference obtained in test involving a sensor film produced of a mixture in which the two component substances were contained at the same 4.5:5.5 ratio as in Example 1. B denotes a curve showing the same relation, obtained with a sensor film containing the two component substances at a ratio of 5:5, C at a ratio of 4:6, D at a ratio of 3.5:6.5. In these curves, the linear portions are inclined slowly and the changes in the potential difference for an increase of the perchlorate ion activity by 10 times the original value were slightly lower. It was, however, ascertained that even with these electrodes, the perchlorate ion activity in the range of from $10^{-1}$ to $10^{-5}$ M could be measured. E denotes a curve obtained with a sensor film containing the component substances at a ratio of 3:6. Although the proportional relation in the case of E between the perchlorate ion activity and the potential difference is lower than that in the case of A, B, C or D, the mixture can practically be used without any obstruction. In the case of the mixture containing the two component substances at a ratio of 6:4 (the results not shown in the graph), it has a disadvantage that the film is dried and solidified at a very low speed, but can also practically be used without any obstruction.

EXAMPLE 3

Figure 7:
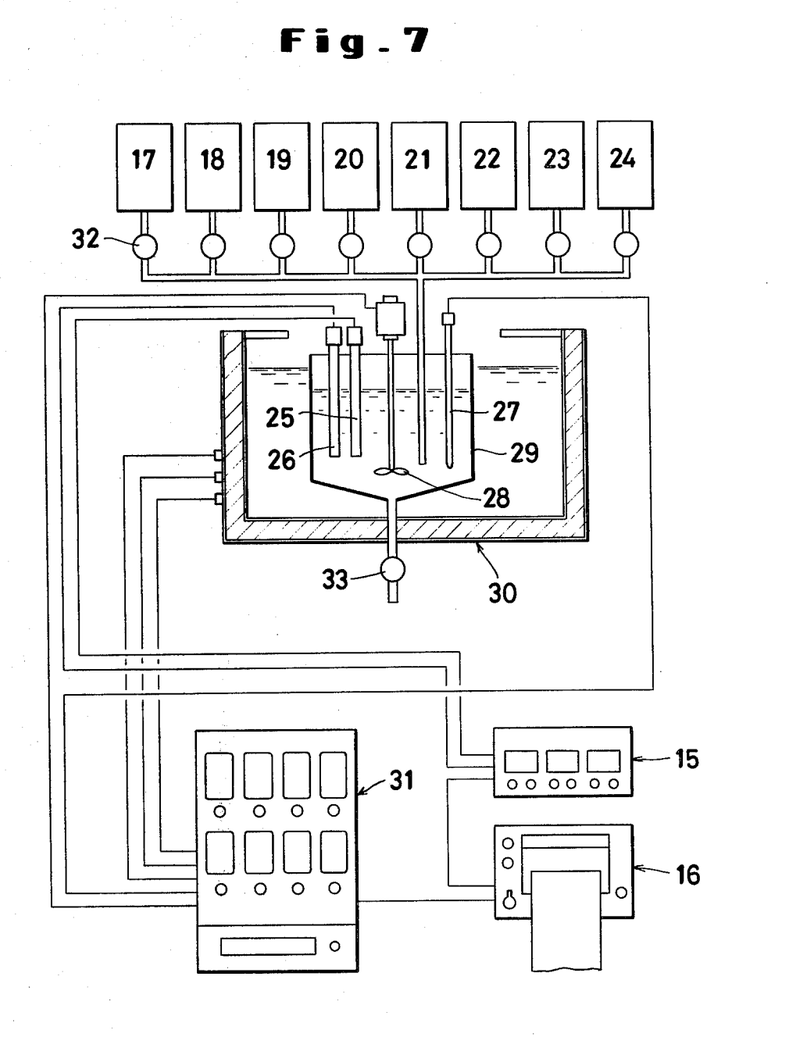
FIG. 7 is a diagram illustrating an automatic electrode testing system used in Example 3.

For the purpose of determining how long (in number of days) the electrodes manufactured by the procedure of Example 1 could be used without entailing any degradation of performance, there were designed and constructed, as illustrated in FIG. 7, a measuring cell 29 having set in position therein tanks 17, 18, 19, 20, 21, 22, 23 and 24 for containing sodium perchlorate solutions of $10^{-1}$ M, $10^{-2}$ M, $10^{-3}$ M, $10^{-4}$ M, $10^{-5}$ M, $10^{-6}$ M, $10^{-7}$ M and pure water respectively, an electrode 25 of the present invention, a reference electrode 26, a temperature control element 27 and a stirrer 28; and an automatic electrode testing system comprising a constant temperature bath 30, a programmer 31, a potentiometer 15 and a recorder 16.

First, from the tank 17 a fixed volume of the perchlorate ion solution of $10^{-1}$ M was introduced through an electromagnetic valve 32 into the measuring cell 29, wherein the solution was stirred by the stirrer 28 and the potential difference between the electrode 25 and the reference electrode 26 was measured by means of the potentiometer 15, with the results of the measurement recorded in conjunction with the solution number on the recorder 16. By the operation of the programmer, the potential difference was continuously recorded for a period of from 1.5 to 2 hours. Then, the solution was discharged through the electromagnetic valve 33. Now, from the tank 18, the perchlorate ion solution of $10^{-2}$ M was similarly introduced into the measuring tank 29 to be subjected to the measurement and recording as described above. While the solutions in the tanks were successively subjected to the measurement and recording in order by the commands from the programmer 31, the solution temperature within the measuring cell 29 was maintained at a fixed temperature of, say, 25° C., by the operation of the temperature control element 27, for example.

When the electrode of the present invention for the measurement of perchlorate ion activity was tested for durability over a prolonged period in the automatic electrode testing system described above, it was ascertained that the electrode still retained its performance intact after 42 days, or about 1000 hours, of continued service.

In the meantime, a conventional electrode using a porous thin film impregnated with an ion-exchange liquid was subjected to the same test. It was confirmed that the electrode performance clearly degraded after about 700 hours. The degradation was so bad that the electrode had to be disassembled, cleaned, reassembled and readjusted. Already at this point, it was quite evident that the electrode manufactured by the present invention would offer a longer service life than the conventional countertype and show no sign of degradation in performance. Then, with the duration of measurement for each solution fixed at about 50 minutes so that all the eight solutions could be subjected once each to the measurement within about eight hours of each work day, the operation of the automatic electrode testing system was repeated day after day. After this daily operation was repeated for a total of about 60 days, the electrode was found to retain its performance intact. This indicates that the electrode of the present invention can be used for a much longer period than the conventional countertype.

EXAMPLE 4

A substance sensitive to nitrate ion was prepared as follows. A mixture of 8 g of tri-n-octyl-methyl ammonium chloride (Capriquat) and 12 g of 1-decanol was placed in a separatory funnel having an inner volume of 100 ml and shaken with 20 ml of an aqueous 0.1 M sodium nitrate solution. The mixture was separated into an organic phase and an aqueous phase. The organic phase was again shaken with 20 ml of the same aqueous 0.1 M sodium nitrate solution. This procedure was repeated a total of three times. The organic phase finally obtained was passed through a dry filter paper to afford a liquid sensitive to nitrate ion. A sensitive substance-Urushi (Japanese lacquer) mixture was obtained by thoroughly mixing 0.05 g of this liquid with 0.05 g of Ise Urushi.

Subsequently, an electrode for the measurement of nitrate ion activity was produced by following the procedure of Example 2.

Figure 8:
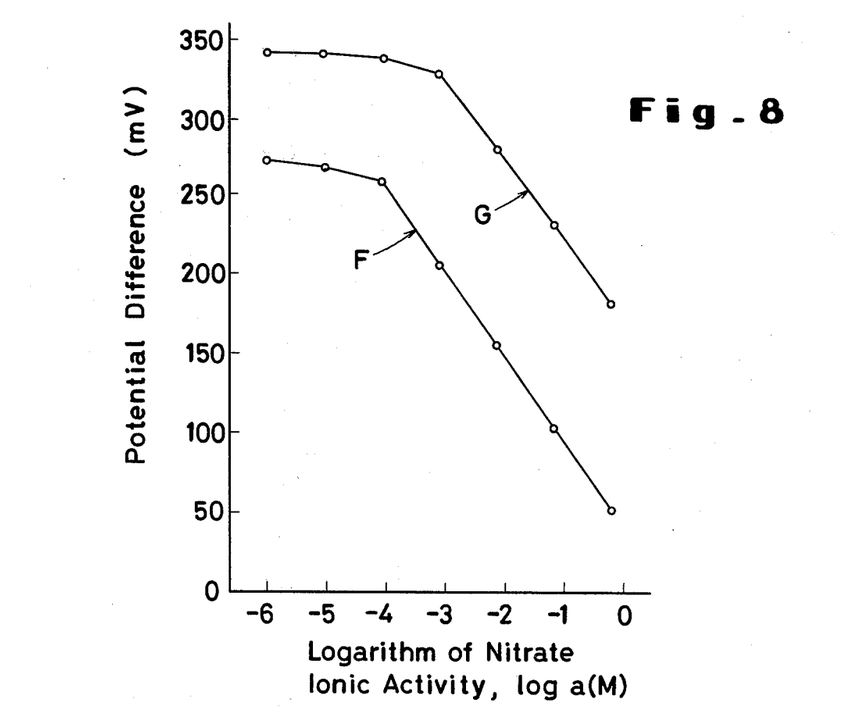
FIG. 8 is a graph showing the results obtained in Examples 4 and 5.

Said sensitive substance-Urushi (Japanese lacquer) mixture was applied to the base 2 and was dried by causing the glass tube to be slowly rotated around its longitudinal axis in a room maintained at a temperature of 60° C. The application of the sensitive substance-Urushi (Japanese lacquer) and the subsequent drying of the applied mixture was repeated a total of three times, to give rise to an electrode of construction like the one shown in FIG. 1. This electrode was used to measure the potential difference of potassium nitrate solutions of varying activity. As the reference electrode, there was used a double-junction reference electrode Model 92-02-00 made by Orion Corp. As the measuring apparatus, there was used a digital ion meter Model 801 made by the same manufacturer. The results of the measurement were as shown by the curve F in the graph of FIG. 8. As is seen from FIG. 8, the electrode of this invention for the measurement of nitrate ion activity generated potential difference having a linear relation with the logarithm of nitrate ion activity within the range of from $10^0$ to $10^{-4}$ M of nitrate ion activity. For an increase of the nitrate ion activity by 10 times the original value, the change in the potential difference generated was about 52 mV when the temperature of the solution under test was 25° C. If this electrode is immersed in a solution with an unknown nitrate ion activity and the potential generated at that electrode is measured, the nitrate ion activity of that solution can easily be determined according to the value of the potential.

EXAMPLE 5

An electrode for the measurement of nitrate ion activity was manufactured by following the procedure of Example 4, except the substance sensitive to nitrate ion was prepared by using 5 g of Capriquat and 15 g of 1-decanol. That is to say, the proportion of Capriquat to 1-decanol was decreased in this example. A sensitive substance-Urushi (Japanese lacquer) mixture was prepared by mixing 0.05 g of the resultant liquid sensitive to nitrate ion and 0.05 g of Ise Urushi. The electrode was manufactured by following the procedure of Example 4. The results of the measurement by use of this electrode were as shown by the curve G in the graph of FIG. 8. It is seen from FIG. 8 that the relation between the logarithm of the nitrate ion activity and the potential difference obtained by this electrode was linear in the range of from $10^0$ to $10^{-3}$ M of nitrate ion activity. Thus, the range was narrower than the range of $10^0$ to $10^{-4}$ M obtained with the electrode of Example 4. The change in the electrode potential for an increase of nitrate ion activity by 10 times the original value was about 48 mV, a value smaller than 52 mV obtained in Example 4.

From the foregoing results, it is learned that the properties of the substance sensitive to nitrate ion to be used in the manufacture of electrode affect the properties of the electrode.

EXAMPLE 6

The liquid sensitive substance marketed by Corning Corp. for use in the electrode, Model 476134, made by the same manufacturer for the measurement of nitrate ion activity is a mixture of an ion exchanger with an intermediate agent. The mixture is composed of tridodecyl-hexadecyl ammonium nitrate and n-octyl-o-nitrophenyl ether. A sensitive substance-Urushi (Japanese lacquer) mixture was prepared by mixing 0.05 g of the resultant sensitive liquid with 0.05 g of Ise Urushi. An electrode was manufactured by using this mixture and following the procedure of Example 4. The results of the measurement obtained by using this electrode were as shown by the curve H in the graph of FIG. 9. In a flat weighing bottle made of glass, 0.15 g of the same sensitive liquid was concentrated at a temperature of 65° C. under pressure of 3 mm Hg, to an eventual amount of 0.05 g. A sensitive substance-Urushi (Japanese lacquer) mixture was prepared by mixing the resultant concentrate with 0.05 g of Ise Urushi. When the measurement was carried out by using an electrode manufactured with this mixture, there were obtained results as shown by the curve I in the graph of FIG. 9.

Under the same conditions, 0.25 g of the same sensitive liquid was concentrated to 0.05 g. The resultant concentrate was mixed with 0.05 g of Ise Urushi. An electrode was manufactured by using the resultant mixture in the same way as described above. The results of the measurement carried out by using this electrode were as shown by the curve J in the graph of FIG. 9.

Figure 9:
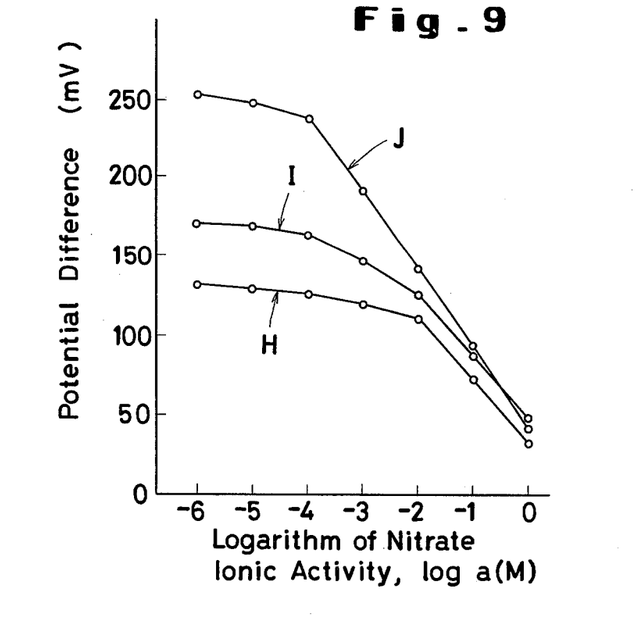
FIG. 9 is a graph showing the results of the measurement performed in Example 6.

It is learned from the results of FIG. 9 that when the sensitive liquid designated for use in the electrode, Model 476134, for the measurement of nitrate ion activity marketed by Corning Corp. is used as the sensitive substance to nitrate ion, the electrode enjoys better performance when the concentration of the ion exchanger present in the liquid is higher. In the case of the electrode which used the liquid having the ion exchanger concentration increased by evaporating the liquid under vacuum to about one fifth the original weight, the linear portion of the curve showing the relation between the logarithm of nitrate ion activity and the potential difference was the range of from $10^0$ to $10^{-4}$ M of nitrate ion activity and the change in the potential for an increase of nitrate ion activity by 10 times the original value was about 48 mV. This means that the electrode possessed substantially the same properties as the electrode manufactured in Example 4. In contrast, the electrodes using the liquid in its original concentration or in a concentration increased to three times the original value showed inferior properties.

EXAMPLE 7

Figure 10:
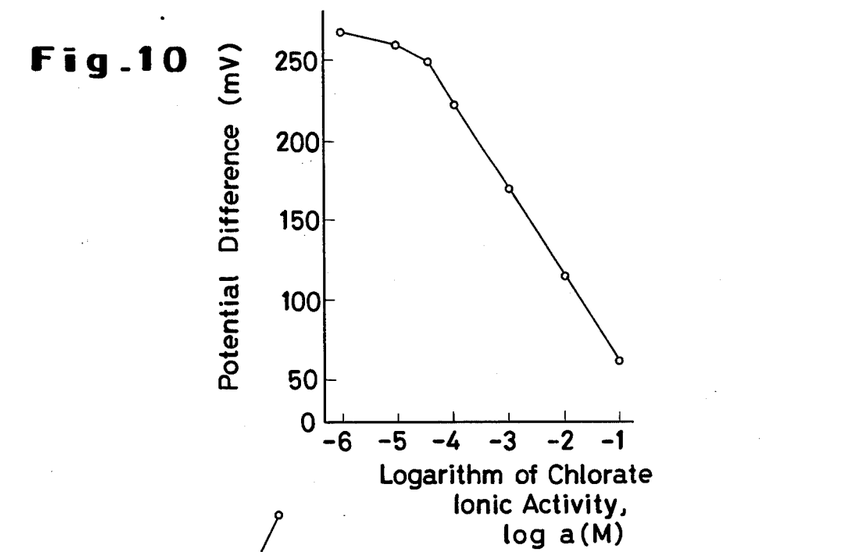
FIG. 10 is a graph showing the results of the measurement performed in Example 7.

By following the procedure of Example 4, a substance sensitive to chlorate ion was prepared. To be specific, a mixture of 8 g of tri-n-octyl-methyl ammonium chloride and 12 g of 1-decanol was shaken with 20 ml of an aqueous 0.1 M sodium chlorate solution to produce a liquid sensitive to chlorate ion. A sensitive substance-Urushi (Japanese lacquer) mixture was made by thoroughly mixing 0.05 g of this liquid with 0.05 g of Ise Urushi. An electrode for the measurement of chlorate activity was manufactured by using this mixture. Sodium chlorate solutions of varying ion activity were tested for potential differences by means of the electrode. The results of the measurement were as shown in FIG. 10. As is clear from FIG. 10, the electrode of this invention for the measurement of chlorate ion activity generated potential differences showing linear relation with the logarithm of chlorate ion activity in the range of from $10^{-1}$ to $3 \times 10^{-5}$ of chlorate ion activity.

This electrode, therefore, can be used for determining the chlorate ion activity of a solution with unknown ionic activity.

EXAMPLE 8

In a volume of water, tetraphenyl borate was added to give a solution of 0.1 M. To this solution, an aqueous 0.1 M potassium sulfate solution was added to produce a white precipitate. The precipitate was the potassium salt of tetraphenyl borate. The precipitate was separated by filtration, washed with water and dried in a desiccator. A 0.01-g portion of the dried precipitate was dissolved in nitrobenzene. A mixture was prepared by adding 0.04 g of the solution to 0.05 g of Ise Urushi. A copper base 4 mm in thickness was attached to the leading end of a plastic tube 12 mm in outside diameter and 120 mm in length and a shielded wire was passed through the interior of the tube and soldered at its leading end to the inner side of said base, to complete an electrode body. The aforementioned mixture was applied in a flat layer to the outer side of the base. The applied mixture was dried by causing the plastic tube to be slowly rotated around its longitudinal axis in a room maintained under controlled conditions of 30° C. of temperature and 80% of relative humidity. By subsequently following the procedure of Example 4, an electrode for the measurement of potassium ion was manufactured.

Figure 11:
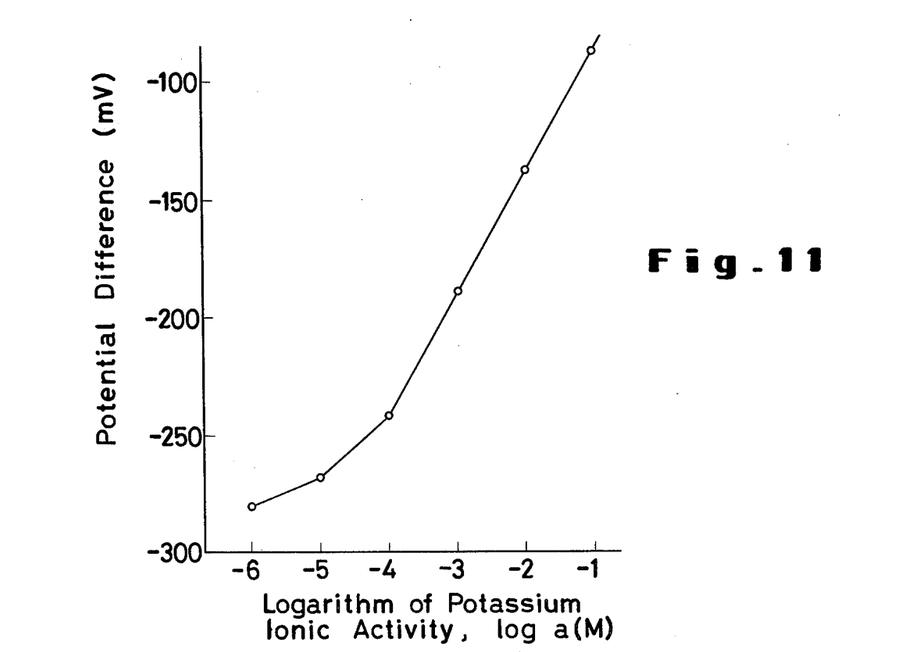
FIG. 11 is a graph showing the results of the measurement performed in Example 8.

This electrode was used to measure the potential of a potassium solution. The results of the measurement were as shown in FIG. 11. The change in the potential of electrode for an increase of potassium activity by 10 times the original value was about 50 mV.

In this example, the conditions for the drying of the applied mixture were 30° C. of temperature and 80% of relative humidity, different from those used in Examples 4 to 7.

EXAMPLE 9

The ion-exchange liquid (containing calcium-dialkyl phosphate) designated for use in the electrode, Model 92-20, marketed by Orion Corp. for the measurement of calcium ion was mixed in the amount of 0.045 g with 0.050 g of Ise Urushi.

Figure 12:
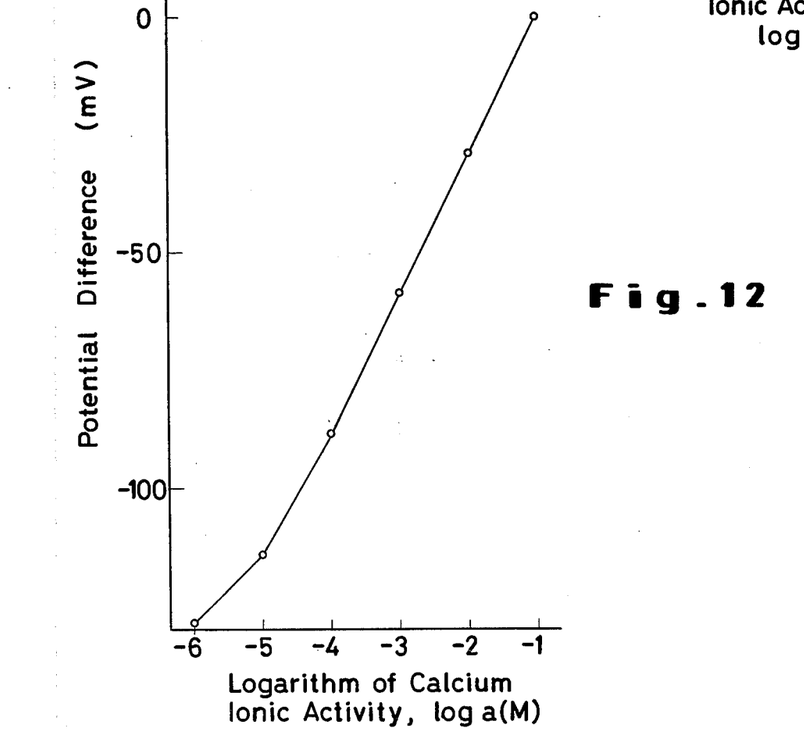
FIG. 12 is a graph showing the results of the measurement performed in Example 9.

A base of graphite 5 mm in thickness was attached to one end of a glass tube 12 mm in outside diameter and 120 mm in length. A shielded wire was passed through the interior of the tube and was connected with the inner side of said base through the medium of an electroconductive paint or a mixture of graphite powder and Ise Urusi, to give rise to an electrode body. The aforementioned sensitive substance-Urushi (Japanese lacquer) mixture was applied to the outer side of the graphite base. By subsequently following the procedure of Example 8, there was manufactured an electrode for the measurement of calcium ion. FIG. 12 shows the results of the measurement carried out by using the electrode.

The change in the potential difference for an increase of calcium ion activity by 10 times the original value was about 30 mV.

In this example, the base of the electrode body to which the sensor film was applied was made of graphite with a view to improving adhesion of the film to the base.

What is claimed is:

1. An electrode for measuring the activity of a selected ion in a solution, which comprises a sensor film having as its principal components a substance sensitive to said selected ion and Urushi.

2. The electrode according to claim 1, wherein said Urushi (Japanese lacquer) contains urushiol as its principal component in an amount of from 50 to 80% by weight.

3. The electrode according to claim 1, wherein the Urushi (Japanese lacquer) content of said sensor film is in the range of from 10 to 97% by weight.

4. The electrode of claim 1, wherein said substance is selected from the group consisting of tri-n-octyl-methyl-ammonium nitrate, dipicrylamine potassium salt, tri-n-octyl-methyl-ammonium iodide, tetraphenyl-ammonium-tetrafluoroborate, tri-n-octylmethyl-ammonium chloride, tris-(4,7-diphenyl-1,10-phenanthroline)-iron(II)-hexafluorophosphate, tri-n-octyl-methyl-ammonium bromide, tri-n-octyl-methyl-ammonium perchlorate, tetraphenyl-phosphonium chromate, tri-dodecyl-hexadecyl-ammonium nitrate, tetraphenyl-phosphonium nitrate, tri-n-octyl-methyl-ammonium chlorate, tri-n-octyl-methyl-ammonium thiocyanate, calcium di-2-ethylhexylphosphate, N-lauryl-N-trialkyl-methyl-amine cyanide, potassium valinomycin, potassium tetraphenylborate, calcium didecylphosphate, methylene blue-thiocyanate, tris-(1,10-phenanthroline)-iron(II)-iodide, tris-(1,10-phenanthroline)-iron(II)-tetrafluoroborate, magnesium di-2-ethylhexylphosphate.

5. A method for the manufacture of an electrode for measuring the activity of a selected ion in a solution, which method comprises the steps of mixing Urushi (Japanese lacquer) with a substance sensitive to said selected ion, applying the resultant mixture to the electrically conductive base of said electrode, and subsequently allowing said applied mixture to set, thereby forming an ion-selective sensor film on said electrode.

6. The method according to claim 5, wherein said Urushi (Japanese lacquer) contains urushiol as its principal component in an amount of from 50 to 80% by weight.

7. The method according to claim 6, wherein the Urushi (Japanese lacquer) content of said sensor film is in the range of from 10 to 97%.

8. The method of claim 5, wherein said applied mixture is set at a temperature of from 20° to 30° C. and a relative humidity of from 70% to 80%.

9. The method of claim 5, wherein said substance is dissolved in an organic solvent and the resultant solution is mixed with said Urushi (Japanese lacquer).

10. The method of claim 9, wherein said organic solvent is selected from the group consisting of nitrobenzene, 1-decanol, 1,2-dichloroethane, chlorobenzene, bromobenzene, glycerol, p-nitrocumene, dinitroethane, dioctylphthalate, n-octyl-2-nitrophenol ether, dioctylphenyl phosphonate and dodecyl alcohol.